(12) United States Patent
Pugin et al.

(10) Patent No.: US 6,248,899 B1
(45) Date of Patent: Jun. 19, 2001

(54) TRANSESTERIFICATION CATALYSTS FIXED TO SOLID SUPPORT MATERIALS

(75) Inventors: Benoît Pugin, Münchenstein; Benoît Dubuis, Muttenz; Adrian Müller, Basel, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/331,286

(22) PCT Filed: Dec. 12, 1997

(86) PCT No.: PCT/EP97/06978

§ 371 Date: Aug. 9, 1999

§ 102(e) Date: Aug. 9, 1999

(87) PCT Pub. No.: WO98/28256

PCT Pub. Date: Jul. 2, 1998

(30) Foreign Application Priority Data

Dec. 20, 1996 (CH) .................................................. 3157/96

(51) Int. Cl.[7] .......................... C07D 249/16; C07C 69/76
(52) U.S. Cl. ............................................. 548/261; 560/61
(58) Field of Search ..................... 560/75, 61; 546/242, 546/188; 548/261

(56) References Cited

U.S. PATENT DOCUMENTS 5,436,357 * 7/1995 Jiang et al. ............................ 556/95
5,561,205 10/1996 Jiang et al. ........................... 526/240

FOREIGN PATENT DOCUMENTS

| 3119643 | 12/1982 | (DE) . |
| 4317428 | 6/1994 | (DE) . |
| 0646567 | 4/1995 | (EP) . |

OTHER PUBLICATIONS

Abstr. for DE 3119643.
Abstr. for DE 4317428.
Angew. Chem., vol. 93, No. 12, (1981), pp. 1092–1093.
Chem. Rev. vol. 93, (1993), pp. 1449–1470.

* cited by examiner

Primary Examiner—Alan L. Rotman
Assistant Examiner—Binta Robinson
(74) Attorney, Agent, or Firm—Luther A. R. Hall

(57) ABSTRACT

A description is given of a process for the transesterification of carboxylic esters, characterized in that the catalyst used is a tin(IV) compound comprising a radical of the formula

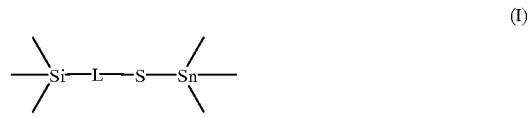

(I)

bound to an inorganic support, where L is an at least divalent radical and at least one of the free valences of the Si in formula (I) is bound to the inorganic support, novel tin(IV) compounds and their preparation.

2 Claims, No Drawings

TRANSESTERIFICATION CATALYSTS FIXED TO SOLID SUPPORT MATERIALS

This application is a 371 of PCT/EP97/06978 filed Dec. 12, 1997.

The present invention relates to immobilized tin-sulfur catalysts, their preparation and their use in transesterification reactions of carboxylic esters.

Transesterification reactions of carboxylic esters can be generally described by the following reaction scheme:

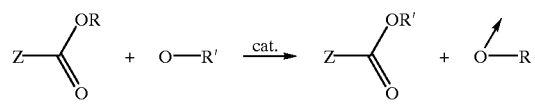

in which R is usually a $C_1$–$C_4$ alkyl radical and R' and Z are each an organic radical. The reaction is an equilibrium reaction. In general, the (lower-boiling) alcohol liberated is distilled off during the reaction. A series of different catalysts for this reaction are known (Junzo Otera, Chem. Rev., 93 (1993) 1449–1470), e.g. acids, bases, amines, metal alkoxides and also, inter alia, organotin compounds. Many of these esterification reactions are carried out at temperatures in the range from 80° C. to above 200° C.

It is economically advantageous if the reactions can be carried out in the melt without solvents. A further advantage is gained if the product does not have to be purified by distillation or extraction after the reaction. For this reason, a catalyst should be able to be used at high temperatures (reaction in the melt) and the catalyzed reaction must not lead to discolored products.

Organotin compounds are known and very mild catalysts for transesterifications of carboxylic esters with alcohols. A problem associated with conventional tin catalysts is achieving an economical separation of the tin from the reaction product. A possible solution is the use of immobilized tin catalysts which can be separated off.

U.S. Pat. No. 5,436,357 discloses, for example, catalysts bound to polystyrene of the type:

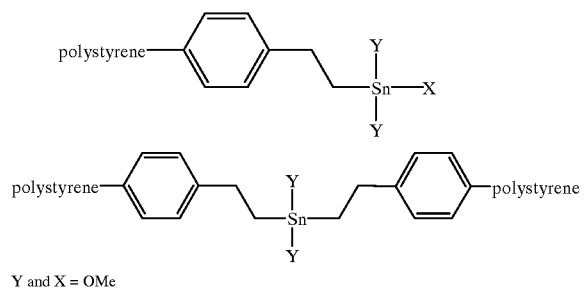

Y and X = OMe
Y = OMe, X = Cl, Br

These compounds are proposed as catalysts for transesterifications in a temperature range of 50–150° C. They can be decanted or filtered off and reused a number of times. In most cases, reuse is associated with a drop in activity. No information is given about Sn leaching, for example as residual tin content of the product.

Furthermore, H. Schuhmann and B. Pachaly, J. Organomet. Chem., 233 (1982) 281–289 and H. Schuhmann and B. Pachaly, Angew. Chem., 93 (1981) 1092–93 have described the preparation of the following compounds which are used stoichiometrically as hydrides for the reduction of alkyl halides.

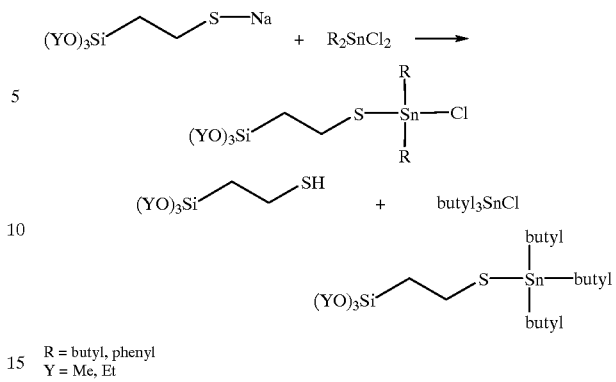

R = butyl, phenyl
Y = Me, Et

These compounds are immobilized on silica gel (or aluminum oxide) and are converted by reduction into the corresponding hydride reagent:

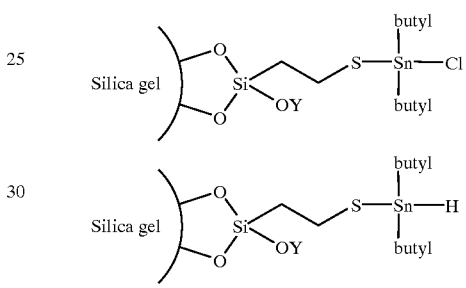

Essentially the same compounds as in the abovementioned publications are described in DE31 19643.

The present invention provides a process for the transesterification of carboxylic esters, characterized in that the catalyst used is a tin(IV) compound comprising a radical of the formula

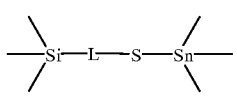

(I)

bound to an inorganic support, where L is an at least divalent radical and at least one of the free valences of the Si in formula (I) is bound to the inorganic support.

These immobilized tin-sulfur catalysts can be used in a wide temperature range and, after the reaction, can be separated from the reaction product simply and completely by solid/liquid separation operations, for example filtration, centrifugation and decantation. The catalysts which have been filtered off continue to be catalytically active and can be reused a number of times.

The process of the invention is particularly suitable for preparing compounds of the general formula

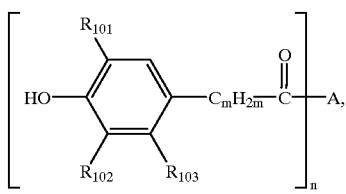

(X)

in which $R_{101}$ and $R_{102}$ are identical or different and are H, alkyl having from 1 to 18 C atoms, phenyl, $C_1$–$C_4$alkyl-substituted phenyl, phenylalkyl having from 7 to 9 C atoms, $C_5$–$C_{12}$cycloalkyl, $C_1$–$C_4$alkyl-substituted $C_5$–$C_{12}$cycloalkyl or a radical

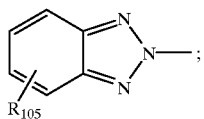

$R_{103}$ is H or $CH_3$;
$R_{105}$ is H, Cl, $SO_3H$ or $C_1$–$C_4$alkyl;
m is 0, 1, 2 or 3; and
n is 1, 2, 3 or 4; where, when n=1,
A is —$OR_{104}$; and
$R_{104}$ is alkyl having from 2 to 45 C atoms, $C_2$–$C_{45}$alkyl interrupted by one or more oxygen, cycloalkyl having from 5 to 12 C atoms, alkenyl having from 2 to 18 C atoms, —$CH_2CHOHCH_2OC(O)R_{109}$ or —$CH_2CH_2$—$OR_{106}$; and
$R_{109}$ is H, alkyl having from 1 to 8 C atoms, alkenyl having from 3 to 5 C atoms or benzyl;
where
$R_{106}$ is

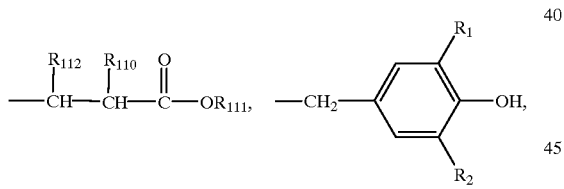

H, alkyl having from 1 to 24 C atoms, phenyl, cycloalkyl having from 5 to 12 C atoms or

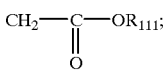

and $R_{110}$ is H or —$CH_3$;
$R_{111}$ is H or alkyl having from 1 to 24 C atoms; and
$R_{112}$ is H or —$CH_3$, with the proviso that $R_{110}$ and $R_{112}$ are not simultaneously —$CH_3$;
or, when n=2,
A is —O—$C_xH_{2x}$—O—, —O—$(CH_2CH_2O)_a$ $CH_2CH_2O$— or —O—$CH_2CH=CHCH_2$—O—; in which
a is from 1 to 30; and
x is from 2 to 20;
or, when n=3, A is

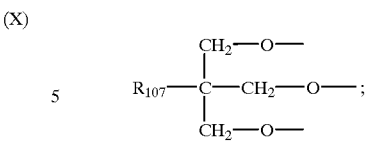

in which $R_{107}$ is alkyl having from 1 to 24 C atoms or phenyl, or, when n=4, A is

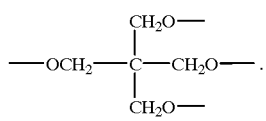

The process is particularly preferred for preparing compounds of the formula (X) in which n is one;

$R_{101}$ is tert-butyl or

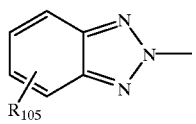

$R_{102}$ is tert-butyl;
$R_{103}$ and $R_{105}$ are H;
m is 2; A is $OR_{104}$;
$R_{104}$ is $(CH_2)_{17}CH_3$, $C_8H_{17}$ (isomer mixture), $C_2$–$C_{45}$alkyl interrupted by one or more oxygen, —$CH_2CHOHCH_2OC(O)R_{109}$; and
$R_{109}$ is alkenyl having from 3 to 5 C atoms;
or n is 2;
$R_{101}$ is tert-butyl or

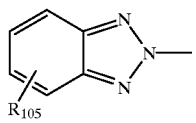

$R_{102}$ is $CH_3$;
$R_{103}$ is H;
m is 2;
A is —O—$(CH_2CH_2O)_aCH_2CH_2O$—; and
a is from 1 to 30;
or n is 3;
$R_{101}$ and $R_{102}$ are tert-butyl;
$R_{103}$ is H;
m is 2; and
A is —O—$CH_2$—$CH(O$—$)$—$CH_2$—O—;
or n is 4;
$R_{101}$ and $R_{102}$ are tert-butyl;
$R_{103}$ is H;
m is 2; and
A is $C(CH_2$—O—$)_4$.

The process of the invention is likewise suitable for preparing compounds of the general formula

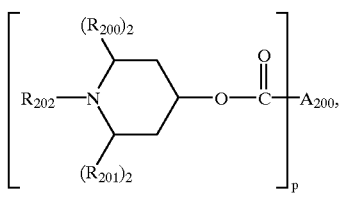

(XX)

in which $R_{200}$ and $R_{201}$ are, independently of one another, $C_1$–$C_4$alkyl;

$R_{202}$ is H, $C_1$–$C_{18}$alkyl, O or $C_1$–$C_{18}$alkoxy;

$A_{200}$ is, when p=1, $C_1$–$C_{12}$alkyl, $C_1$–$C_{12}$alkyl substituted by —C(O)OH or $C_2$–$C_5$alkenyl;

or, when p=2, $C_1$–$C_{12}$alkylene; and p is 1 or 2.

The process of the invention is likewise suitable for preparing compounds which are obtainable by reaction of a compound of the formula

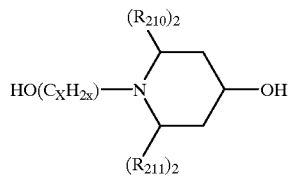

(XXX)

in which $R_{210}$ and $R_{211}$ are, independently of one another, $C_1$–$C_4$alkyl; and x is from 1 to 12;

with a compound of the formula

 $R_{212}OC(O)$—$A_{210}$—$(O)COR_{213}$ (XXXI)

in which $R_{212}$ and $R_{213}$ are, independently of one another, $C_1$–$C_4$alkyl; and $A_{210}$ is $C_1$–$C_{12}$alkylene.

The compounds obtainable by reaction of the compounds (XXX) with (XXXI) are, in general, oligomeric or polymeric compounds or mixtures of such compounds. The stoichiometric ratios and reaction parameters make it possible to influence the formation of the compounds or mixtures of compounds.

Examples of the substituents in the formulae (X), (XX), (XXX) and (XXXI) are given below.

Alkyl having up to 45 C atoms can be a linear or branched alkyl group and can be, for example: methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl, eicosyl, henicosyl, docosyl, triacontyl and others. Preference is given to alkyl having 1–12 C atoms and particular preference is given to alkyl having 1–8 C atoms. When mention is made of i-$C_8H_{17}$, this is to be understood as including a mixture of isomers.

A very particularly preferred example of $R_{101}$ and $R_{102}$ is the t-butyl group. Preference is also given to $R_{101}$=—$CH_3$ and $R_{102}$=t-butyl or $R_{101}$=isopropyl and $R_{102}$=t-butyl. As $R_{103}$, preference is given to —H. Preferred $R_{111}$, $R_{107}$ and $R_{106}$ are alkyl groups having from 1 to 18 C atoms.

Examples of cycloalkyl substituents having from 5 to 12 C atoms are cyclopentyl, cyclohexyl, cycloheptyl, cyclooctyl, cyclodecyl and cyclododecyl. Preference is given to cyclohexyl.

Examples of $C_1$–$C_4$alkyl-substituted cycloalkyl having from 5 to 12 C atoms are 2- or 4-methylcyclohexyl, dimethylcyclohexyl, trimethylcyclohexyl and t-butylcyclohexyl.

Examples of $C_1$–$C_4$alkyl-substituted phenyl substituents are methylphenyl, dimethylphenyl, trimethylphenyl, ethylphenyl, diethylphenyl, isopropylphenyl and 6-butylphenyl.

Examples of phenylalkyl having from 7 to 9 C atoms are benzyl, phenethyl, α-methylbenzyl and α,α-dimethylbenzyl. Preference is given to benzyl.

Alkenyl having up to 18 C atoms is, for example, vinyl, propenyl, allyl, butenyl, methallyl, hexenyl, decenyl or heptadecenyl.

When m=2, the group described is, for example, —$CH_2$—$CH_2$—; when m=3, the group described is, for example, —$CH_2$—$CH_2$—$CH_2$— or —$CH_2CH(CH_3)$—.

The tin(IV) compounds which can be used as catalysts in the process of the invention are, in general, mixtures of compounds of various compositions. Preference is given to compounds or mixtures of compounds obtainable by reaction of a compound of the formula:

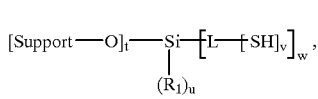

(IIa)

in which t is 1, 2 or 3;

u is 0, 1 or 2;

v is 1, 2, 3, 4, 5, 6, 7, 8 or 9; and w is 1, 2 or 3, with the proviso that t+u+w=4;

L is an at least divalent $C_1$–$C_{18}$alkylene, $C_2$–$C_{18}$alkenylene, phenylene, $C_1$–$C_{18}$alkylenephenylene radical or $C_2$–$C_{18}$alkylene or $C_1$–$C_{18}$alkylene/phenylene radical interrupted by one or more O, C(O), S, C(S), N(Y), C(O)—N(Y), N(Y)—C(O)—N(Y) and/or N(Y)—C(O)—O;

Support is an inorganic support material;

$R_1$ are, independently of one another, $C_1$–$C_4$alkoxy, phenoxy, $C_1$–$C_4$alkyl, phenyl or halogen; and Y are, independently of one another, $C_1$–$C_{18}$alkyl, phenyl or $C_1$–$C_{18}$alkyl/phenyl; with a compound of the formula $Sn[R_2]_4$ (IIb), in which $R_2$ are, independently of one another, $C_1$–$C_{18}$alkyl, substituted $C_1$–$C_{18}$alkyl, $C_2$–$C_{18}$alkenyl, $C_1$–$C_{18}$haloalkyl, $C_6$–$C_{16}$haloaryl, $C_3$–$C_{16}$haloheteroaryl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_{12}$hydroxyalkyl, $C_3$–$C_8$cycloalkyl, $C_6$–$C_{16}$aryl, substituted $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, —Cl, —Br, —I, OH, —O$C_1$–$C_{18}$alkyl, —O$C_6$–$C_{16}$aryl, —OOC—$C_1$–$C_{18}$alkyl, —OOC—phenyl, SH, —N(Si($CH_3$)$_3$)$_2$, S$C_1$–$C_{18}$alkyl, —$SC_6$–$C_{16}$aryl, —$SC(O)$—$C_1$–$C_{18}$alkyl, —$SC(O)$—phenyl, —$SC(S)$—$C_1$–$C_{18}$alkyl, —$SC(S)$—phenyl, H or an oxygen bridge to a further Sn atom;

or two radicals $R_2$ are together =S or =O, with the proviso that at least one $R_2$ radical which can react with an SH group to form an S—Sn bond is present.

L is preferably $C_1$–$C_{18}$alkylene, $C_2$–$C_{18}$alkenylene, phenylene or $C_1$–$C_{18}$alkylene/phenylene, particularly preferably $C_1$–$C_{18}$alkylene, very particularly preferably $C_2$–$C_6$alkylene.

$R_1$ is preferably $C_1$–$C_4$alkoxy, particularly preferably methoxy or ethoxy.

$R_2$ is preferably halogen, OH or =O, particularly preferably chlorine.

Examples of an at least divalent $C_1$–$C_{18}$alkylene radical are linear or branched $C_1$–$C_{18}$alkylene radicals of the type mentioned further below in which at least one further H atom is replaced by a direct bond, for example —$CH_2$—, —$CH_2CH_2$—, —$C(CH_3)_2$—, —$CH_2C(CH_3)CH_2$—, =CH— or —$CH_2CHCH_2$—.

At least divalent $C_2$–$C_{18}$alkenylene radicals are analogous to the at least divalent alkylene radicals described; they have one or more C—C double bonds. Examples of at least divalent phenylene radicals are o-phenylene or p-phenylene.

At least divalent $C_1$–$C_{18}$alkylene/phenylene radicals are derived from the at least divalent alkylene radicals described by the alkylene chain being interrupted by phenylene, where phenylene can also form the beginning and/or the end of the chain.

At least divalent $C_2$–$C_{18}$alkylene or $C_2$–$C_{18}$alkylene/phenylene radicals interrupted by one or more O, C(O), S, C(S), N(Y), C(O)—N(Y), N(Y)—C(O)—N(Y) and/or N(Y)—C(O)—O are derived from the analogous at least divalent radicals described; in the case of a plurality of interrupting radicals, these are generally not directly adjacent. Examples of radicals of this type in which the interrupting radicals can also form the beginning and/or the end of the chain are: —$CH_2CH_2$—O—$CH_2$—$CH_2$—, —$CH_2$—$C_6H_4$—$CH_2$—O—$CH_2$—, —$CH_2$—$CH_2$—C(O)—$CH_2$, —$CH_2$—$CH_2$—C(O), —$CH_2$—CH—$CH_2$—$CH_2$—N($C_2H_5$)—$CH_2$—$CH_2$—O— or —$CH_2$—$CH_2$—CH—$CH_2$—O—$CH_2$—$CH_2$—O—.

Trivalent alkylene radicals L are, for example,

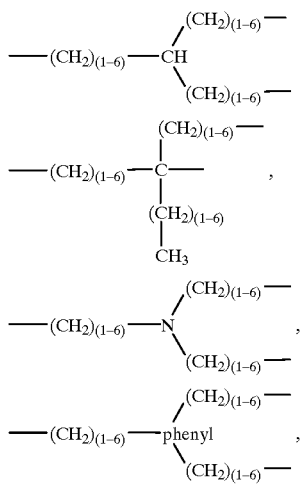

with the proviso that the sum of the C atoms is not more than 18.

In the above definitions, halogen is to be understood as being fluorine, chlorine, bromine or iodine. In the case of a plurality of halogen substituents, these can be of the same type or mixed (for example Cl and F).

Alkyl is methyl, ethyl, isopropyl, n-propyl, n-butyl, iso-butyl, sec-butyl, tert-butyl or the various isomeric pentyl, hexyl, heptyl, octyl, nonyl, decyl, undecyl or dodecyl radicals. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl or 2,2,2-trichloroethyl; preferably trichloromethyl, difluorochloromethyl, trifluoromethyl or dichlorofluoromethyl.

Alkoxy is, for example, methoxy, ethoxy, propyloxy, i-propyloxy, n-butyloxy, i-butyloxy, s-butyloxy or t-butyloxy; preferably methoxy or ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy; preferably difluoromethoxy, 2-chloroethoxy or trifluoromethoxy.

Cycloalkyl is, for example, cyclopropyl, dimethylcyclopropyl, cyclobutyl, cyclopentyl, methylcyclopentyl, cyclohexyl or cycloheptyl, preferably cyclopropyl, cyclopentyl or cyclohexyl.

Alkoxyalkyl is, for example: methoxymethyl, ethoxymethyl, propyloxymethyl, methoxyethyl, ethoxyethyl, propyloxyethyl, methoxypropyl, ethoxypropyl or propyloxypropyl.

Phenyl, including phenyl as part of a substituent such as phenoxy, phenylthio, phenoxycarbonyl, phenylaminocarbonyl, benzyl or benzoyl, can in general be present in unsubstituted form or be substituted by further substituents. The substituents can then be in the ortho, meta and/or para positions. Preferred substituent positions are the ortho and para positions relative to the ring linkage point. Preferred substituents are halogen atoms.

Aralkyl is, for example, benzyl, phenylethyl, 3-phenylpropyl, a-methylbenzyl, phenylbutyl or α,α-dimethylbenzyl.

Aryl and analogously haloaryl are, for example, phenyl, tetralin, indene, naphthalene, azulene or anthracene.

Heteroaryl and analogously haloheteroaryl are, for example, pyrrole, furan, thiophene, oxazole, thiazole, pyridine, pyrazine, pyrimidine, pyridazine, indole, purine, quinoline or isoquinoline.

Heterocycloalkyl is, for example, oxirane, oxetane, azetidine, azirine, 1,2-oxathiolane, pyrazoline, pyrrolidine, piperidine, piperazine, morpholine, dioxolane, tetrahydropyran, tetrahydrofuran or tetrahydrothiophene.

The inorganic support materials are preferably glass, silicates, semimetal oxides and metal oxides which are particularly preferably in the form of powder having a mean particle diameter of from 10 nm to 5 mm. The particles can be compact or porous. Porous particles preferably have a high internal surface area, for example 1–1200 $m^2/g$. Further preferred support materials are inorganic support materials containing OH groups. Examples of oxides and silicates are $SiO_2$, $TiO_2$, $ZrO_2$, MgO, NiO, $WO_3$, $Al_2O_3$, $La_2O_3$, silica gels, clays and zeolites. Particularly preferred support materials are silica gels, aerosils, aluminum oxide, titanium oxide and mixtures thereof. An example of glass as support material is "controlled pore glass", which is commercially available.

A further aspect of the present invention is a tin(IV) compound comprising a radical of the formula

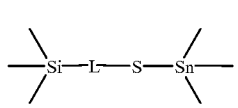
(I)

bound to an inorganic support, where L is an at least divalent radical and at least one of the free valences of the Si in formula (I) is bound to the inorganic support, with the exception of tin(IV) compounds which have two or three hydrocarbon radicals on the Sn and only one tin-sulfur bond and the Si is bound via the three free valences to an OH-containing inorganic support.

Preferred immobilized tin(IV) compounds comprise a radical of the formula (Ia)

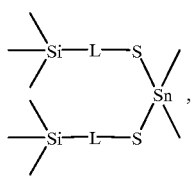

in which L is a divalent radical and at least one of the free valences of each Si in formula (Ia) is bound to the inorganic support.

Likewise preferred immobilized tin(IV) compounds are those which comprise a radical of the formula (Ib)

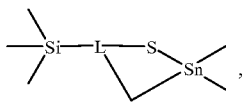
(Ib)

in which L is a trivalent radical and at least one of the free valences of Si in formula (Ib) is bound to the inorganic support. The meanings of L, including the preferences, are indicated above.

Preference is also given to immobilized tin(IV) compounds or mixtures of compounds obtainable by reaction of a compound of the formula:

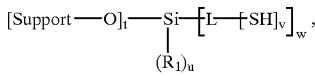
(IIa)

in which
t is 1, 2 or 3;
u is 0, 1 or 2;
v is 1, 2, 3, 4, 5, 6, 7, 8 or 9; and
w is 1, 2 or 3,
with the proviso that t+u+w=4;
L is an at least divalent $C_1$–$C_{18}$alkylene, $C_2$–$C_{18}$alkenylene, phenylene,
$C_1$–$C_{18}$alkylene/phenylene radical or $C_2$–$C_{18}$alkylene or $C_1$–$C_{18}$alkylene/phenylene radical interrupted by one or more O, C(O), S, C(S), N(Y), C(O)—N(Y), N(Y)—C(O)—N(Y) and/or N(Y)—C(O)—O;
Support is an inorganic support material:
$R_1$ are, independently of one another, $C_1$–$C_4$alkoxy, phenoxy, $C_1$–$C_4$alkyl, phenyl or halogen; and
Y are, independently of one another, $C_1$–$C_{18}$alkyl, phenyl or $C_1$–$C_{18}$alkyl/phenyl; with a compound of the formula $$Sn[R_2]_4 \quad (IIb),$$

in which $R_2$ are, independently of one another, $C_1$–$C_{18}$alkyl, substituted $C_1$–$C_{18}$alkyl, $C_2$–$C_{18}$alkenyl, $C_1$–$C_{18}$haloalkyl, $C_6$–$C_{16}$haloaryl, $C_3$–$C_{16}$haloheteroaryl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_{12}$hydroxyalkyl, $C_3$–$C_8$cycloalkyl, $C_6$–$C_{16}$aryl, substituted $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, —Cl, —Br, —I, OH, —O$C_1$–$C_{18}$alkyl, —O$C_6$–$C_{16}$aryl, —OOC—$C_1$–$C_{18}$alkyl, —OOC—phenyl, SH, —N(Si(CH$_3$)$_3$)$_2$, S$C_6$–$C_{18}$alkyl, —S$C_6$—$C_{16}$aryl, —SC(O)—$C_1$–$C_{18}$alkyl, —SC(O)—phenyl, —SC(S)—$C_1$–$C_{18}$alkyl, —SC(S)—phenyl, H or an oxygen bridge to a further Sn atom;

or two radicals $R_2$ together are =S or =O, with the proviso that at least one $R_2$ radical which can react with an SH group to form an S—Sn bond is present.

Preferably, t is 2 or 3, u is 0 or 1, v is 1 or 2 and w is 1 or 2.

Examples of compounds comprising a radical of the formula (I) or of compounds obtainable by reaction of compounds of the formulae (IIa) and (IIb) are:

Support⌇Si—L—S—Sn(R$_2$)$_3$;

Support⌇Si—L—S
　　　　　　　　＼
　　　　　　　　　Sn(R$_2$)$_2$;
　　　　　　　　／
Support⌇Si—L—S

L———S
　　　　　　　／　　　＼
Support⌇Si—L—S—Sn(R$_2$)$_2$;

L———S
　　　　　　　／　　　＼
Support⌇Si—L—S—Sn(R$_2$)$_2$;
　　　　　　　＼
　　　　　　　　L—SH

Support⌇Si—L—S—Sn(R$_2$)$_2$;
　　　　　　　＼　／
　　　　　　　　S

S
　　　　　　　　／　＼
Support⌇Si—L—S—Sn(R$_2$)$_2$;
　　　　　　　＼　／
　　　　　　　　S

L—S—Sn(R$_2$)$_3$;
　　　　　　　／
Support⌇Si—L—S
　　　　　　　＼
　　　　　　　　Sn(R$_2$)$_2$;
　　　　　　　／
Support⌇Si—L—S
　　　　　　　＼
　　　　　　　　L—SH Support⌇Si is the bond to the inorganic support material and any further radicals $R_1$ bound to Si, with the proviso that the total number of bonds on the Si is 4.

Support ~~~ Si can be illustrated by

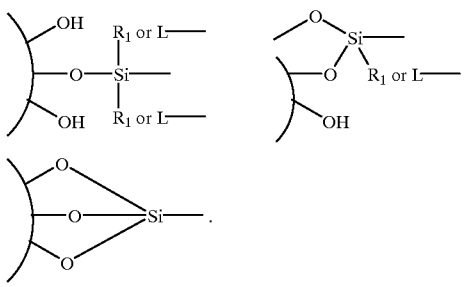

In general, no uniform bond is obtained.

A further aspect of the present invention is the preparation of the tin(IV) compounds bound to (immobilized on) an inorganic support which are according to the invention or can be used according to the invention. This can be carried out in various ways which are known in principle. In the following, two basic methods of preparation are described by way of example.

Method 1: A thiol is first immobilized and the immobilized thiol is subsequently reacted with a tin(IV) compound.

Immobilization of the thiol:

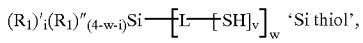

in which

L, v and w are as defined above, including the preferences;

$R_1'$ is $C_1$–$C_4$alkyl or phenyl;

$R_1''$ are, independently of one another, $C_1$–$C_4$alkoxy, phenoxy or halogen; and i is 0, 1 or 2, with the proviso that w+i is less than 4.

The immobilization of alkoxy silanes and halosilanes on an inorganic support has been comprehensively described in the literature (for example by: K. K. Unger, Porous Silica, in Journal of Chromatography Library, Vol 16, Elsevier Scientific Publishing Company (1979)). The loading density (mmol of thiol/g of support) of the Si thiol can be controlled within a wide range by means of the amount of Si thiol used relative to the amount of support used and by means of the immobilization conditions. The Si thiol compound is usually dissolved in a solvent (e.g. xylene, toluene, benzene, THF, methylene chloride, ethyl acetate or ether). Preference is given to nonpolar and high-boiling solvents. This solution is then added to the support (or vice versa) and the mixture is typically stirred gently for 3–50 hours, preferably for about 10–20 hours, at temperatures of from 50° C. to the reflux temperature. The water formed or the alcohol formed is distilled off. The product is then filtered off and washed with a suitable solvent (e.g. alcohol) to remove any excess thiol. The product can subsequently be dried at elevated temperature, preferably under reduced pressure, or it can be directly, without drying, slurried in a solvent suitable for the reaction with Sn(IV) compounds. To prevent possible oxidation of the thiol to corresponding disulfides, the procedure can be carried out under inert gas (e.g. nitrogen, argon) if necessary.

It is also possible to obtain thiol-containing solids (polysiloxanes) by condensation of "Si thiol" compounds either alone or together with alkoxysilanes. Examples are given in DE 30 29 599 (crosslinking of metal-phosphine-Si(OR)$_3$ complexes with H$_2$O to give polysiloxanes and also crosslinking of phosphine-Si(OR)$_3$ to give polysiloxanes and subsequent formation of metal complexes). A review may be found, for example, in C. J. Brinker, G. W. Scherrer, Buch: Sol Gel Science, Academic Press (1990).

The immobilized thiols are subsequently reacted with Sn(IV). (General literature on the preparation of Sn compounds having Sn—S bonds: Gmelin, 8th edition, tin). These can be either pure Sn(R$_2$)$_4$ compounds or mixtures of various Sn(R$_2$)$_4$ compounds. The 4 radicals R$_2$ can be identical or different. At least one R$_2$ has to be a radical which can react with a thiol group to form an S—Sn bond. Compounds having a radical R$_2$ of this type are preferably halides, alkoxides, carbonates or Sn compounds having OH or Sn=O groups. It is also known that Sn(alkyl)$_4$ compounds can react with thiols to form an Sn-S bond. The Sn(IV) compound is generally dissolved in a suitable solvent (e.g. linear and cyclic alkanes, aromatics such as benzene or toluene, halogenated hydrocarbons, nitromethane, DMSO, alcohols, acetone, carboxylic acids such as acetic acid, esters, DMF, nitrites and also water) and the solution is added to the Si thiol fixed on the support, or vice versa. The addition can be carried out at temperatures of from −78° C. to 100° C. In the case of Sn-halogen compounds, the reaction with the Si thiol can result in liberation of hydrohalic acid. This can be neutralized by means of bases (for example alkalis, carbonates, ammonia, amines). After the Sn(IV) compound(s) and the Si thiol have been combined, the reaction mixture is stirred slowly at temperatures of from 20° C. to the boiling point of the solvent. The reaction time is typically from 1 hour to a number of days. The product is then filtered off, washed with solvents such as alcohols, water, and, if necessary, after-treated with a slightly basic aqueous solution or a solution which modifies the ligand or ligands. The ratio of S to Sn can be controlled via the amount of Sn(IV) which is added relative to the amount of thiol immobilized on the support. The ratio of S/Sn can vary in the range from 1:1 to 10:1.

The ratio of S/Sn can also be changed afterwards by coproportionation with an Sn(IV) compound.

The immobilized catalysts can be used without drying or they can be dried at elevated temperature (preferably under reduced pressure) before use and, if necessary, also be thermally treated before use, for example at a temperature in the range 100° C.–300° C.

Instead of the immobilization of thiols, it is also possible to immobilize disulfides, for example of the following types, in the manner described above for the thiols:

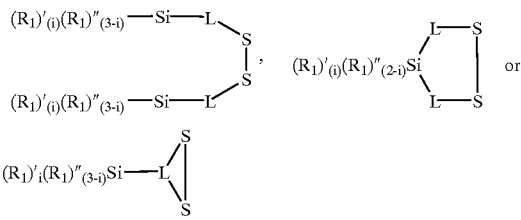

in which the substituents are as defined above, including their preferences, and i is 1–3.

Such disulfides are known or can be prepared in a simple way by known methods (W. Buder, Z. Naturforsch., 34b (1979) 790–793). Some of them are commercially available and are described, for example, in the company document "Chemieforschung im Degussa Forschungszentrum Wolfgang", Volume 1, pages 94–99, 1988.

The immobilized disulfides can subsequently be either a) reacted directly with Sn compounds:

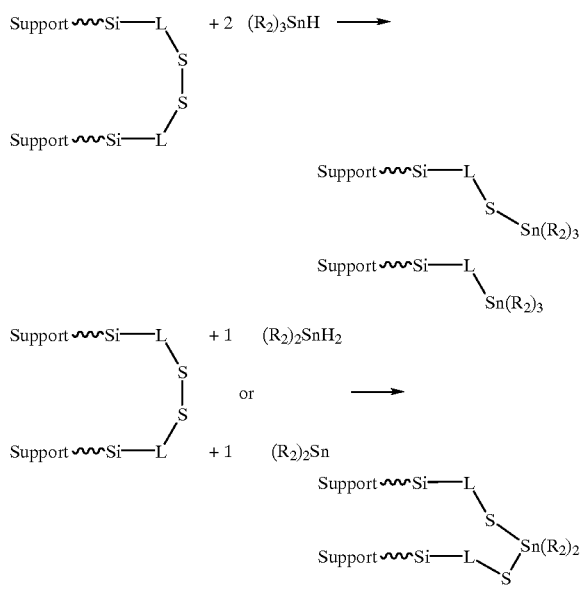

or
b) first reduced to thiols or thiolates (e.g. using $Na_2S$, $K_2S$, glucose, sodium dithionite, phosphine) and subsequently reacted with Sn(IV) compounds as described for the thiols.

The invention therefore also provides a process for preparing compounds of the formula (I) according to claim 1 immobilized on inorganic supports by reacting a compound of the formula:

$$[Support-O]_t-\underset{(R_1)_u}{Si}-[L-[SH]_v]_w, \quad (IIa)$$

in which
t is 1, 2 or 3;
u is 0, 1 or 2;
v is 1, 2, 3, 4, 5, 6, 7, 8 or 9; and
w is 1, 2 or 3,
with the proviso that t+u+w=4;
L is an at least divalent $C_1$–$C_{18}$alkylene, $C_2$–$C_{18}$alkenylene, phenylene,
$C_1$–$C_{18}$alkylene/phenylene radical or a $C_2$–$C_{18}$alkylene or $C_1$–$C_{18}$alkylene/phenylene radical interrupted by one or more O, C(O), S, C(S), N(Y), C(O)—N(Y), N(Y)—C(O)—N(Y) and/or N(Y)—C(O)—O;
Support is an inorganic support material;
$R_1$ are, independently of one another, $C_1$–$C_4$alkoxy, phenoxy, $C_1$–$C_4$alkyl, phenyl or halogen; and
Y are, independently of one another, $C_1$–$C_{18}$alkyl, phenyl or $C_1$–$C_{18}$alkyl/phenyl; with a compound of the formula $$Sn[R_2]_4 \quad (IIb),$$

in which
$R_2$ are, independently of one another, $C_1$–$C_{18}$alkyl, substituted $C_1$–$C_{18}$alkyl, $C_2$–$C_{18}$alkenyl, $C_1$–$C_{18}$haloalkyl, $C_6$–$C_{16}$haloaryl, $C_3$–$C_{16}$haloheteroaryl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_{12}$hydroxyalkyl, $C_3$–$C_8$cycloalkyl, $C_6$–$C_{16}$aryl, substituted $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, —Cl, —Br, —I, OH, —$OC_1$–$C_{18}$alkyl, —$OC_6$–$C_{16}$aryl, —OOC—$C_1$–$C_{18}$alkyl, —OOC-phenyl, SH, —$N(Si(CH_3)_3)_2$, $SC_1$–$C_{18}$alkyl, —$SC_6$–$C_{16}$aryl, —SC(O)—$C_1$–$C_{18}$alkyl, —SC(O)-phenyl, —SC(S)—$C_1$–$C_{18}$alkyl, —SC(S)-phenyl, H or an oxygen bridge to a further Sn atom;
or two radicals $R_2$ are together =S or =O,
with the proviso that at least one $R_2$ radical which can react with an SH group to form an S—Sn bond is present.

Method 2: Firstly preparation of an, if desired isolated, immobilized Sn—S compound and then immobilization of this compound. (General literature on the preparation of Sn compounds having Sn—S bonds: Gmelin, 8th edition, tin).

Pure immobilized Sn—S compounds or mixtures thereof are obtained by reacting n° compounds of the type Si—SM having n°•v•w SM groups either partially or completely with compounds $Sn(R_2)_4$ so as to form at least one Sn—S bond.

$$n° \quad (R_1)'_i(R_1)''_{(4-i-w)}Si-[L-[S-M]_v]_w \quad \text{"Si—SM"}$$

$$\downarrow Sn(R_2)_4$$

Immobilizable Sn—S compounds
The substituents and the indices i, v and w are as defined above, including their preferences, M is H or an alkali metal, preferably Na, K or Li, and n° is 1–4, preferably 1–3.
Examples of the compounds formed are shown below.

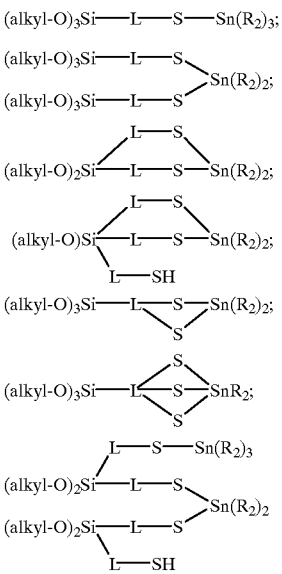

If at least one $R_2$ is halogen, the immobilizable Sn—S compounds are prepared by reaction of the thiol or a thiolate with $Sn(R_2)_4$. In the reaction with the thiol, the hydrohalic acid formed can be neutralized by means of a base (e.g. alkalis, carbonates, ammonia, amines).

If at least one $R_2$ is O-alkyl, O-aryl, OH or $N(alkyl)_2$ or two $R_2$ are together a double bond to oxygen, the immobilizable Sn—S compounds are prepared by reaction of the thiol with $Sn(R_2)_4$. If necessary, the HO-alkyl, HO-aryl, $H_2O$ or amine formed during the reaction can be distilled off.

It is also known that $Sn(alkyl)_4$ compounds can react with thiols to form an Sn—S bond (Gmelin).

Where a plurality of $R_2$ can react with the thiol/thiolate, the preferred stoichiometry on the Sn can be set by selection of the thiol/Sn ratio.

The immobilizable Sn—S compounds can be immobilized on a support or polycondensed in a manner analogous to that for the thiol compounds (see Method 1).

The invention therefore likewise provides a further process for preparing a tin(IV) compound bound to an inorganic support, characterized in that a compound of the formula

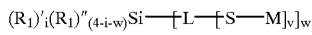

$$(R_1)'_i(R_1)''_{(4-i-w)}Si\text{—}[L\text{—}[S\text{—}M]_v]_w$$

is reacted with a compound of the formula $Sn(R_2)_4$ to form an immobilizable Sn—S compound and this compound is immobilized on an inorganic support,
where
 $(R_1)'$ is $C_1$–$C_4$alkyl or phenyl;
 $(R_1)''$ are, independently of one another, $C_1$–$C_4$alkoxy, phenoxy or halogen; and
 i is 0, 1 or 2, with the proviso that w+i is less than or equal to 4;
 v is 1, 2, 3 or 4; and
 w is 1, 2 or 3;
 L is an at least divalent $C_1$–$C_{18}$alkylene, $C_2$–$C_{18}$alkenylene, phenylene,
 $C_1$–$C_{18}$alkylene/phenylene radical or a $C_2$–$C_{18}$alkylene or $C_1$–$C_{18}$alkylenelphenylene radical interrupted by one or more O, C(O), S, C(S), N(Y), C(O)—N(Y), N(Y)—C(O)—N(Y) and/or N(Y)—C(O)—O;
 Support is an inorganic support material;
 $R_2$ are, independently of one another, $C_1$–$C_4$alkoxy, phenoxy, $C_1$–$C_4$alkyl, phenyl or halogen; and
 Y are, independently of one another, $C_1$–$C_{18}$alkyl, phenyl or $C_1$–$C_{18}$alkyl/phenyl;
 n° is 1, 2, 3 or 4; and
 M is H or an alkali metal.

After the immobilization, the immobilized catalysts can be used without drying or can be dried at elevated temperature (preferably under reduced pressure) before use and can, if necessary, also be thermally treated before use (at temperatures in the range 100° C.–300° C.).

The catalyst can be present in dispersed form in the reactants and is filtered off after the reaction is complete. The catalyst which has become exhausted by use can be regenerated and reused or else can be discarded. It is also possible to arrange the catalyst in a fixed bed and to carry out the reaction in, for example, a flow reactor (continuous process).

The transesterification is advantageously carried out by reacting the starting materials either in the form of a solution in a solvent or, if they are not liquid, in the form of a melt produced by increasing the temperature.

Solvents employed are the compounds and mixtures which are customary per se, for example aromatic hydrocarbons such as benzene and alkyl-substituted or halogenated benzenes, in particular toluene, xylene or dichlorobenzene, high-boiling aliphatic hydrocarbons such as high-boiling paraffins, aprotic solvents such as dimethylformamide or dimethylaniline.

The catalyst is added to the reaction mixture in amounts of, for example, from 0.001 to 10 mol %, advantageously from 0.01 to 1 mol %, of active material, based on the compounds comprising a radical of the formula (I).

The ratio of carboxylic ester and alcohol in the reaction mixture is not critical and can be, for example, from 0.8 to 1.3 mol of the carboxylic ester per equivalent of the alcohol.

The reaction temperature can be, for example, from 110 to 250° C., preferably from 130 to 210° C.

The transesterification of the carboxylic esters generally takes from 1 to 10 hours, advantageously from 1 to 5 hours and preferably from 1 to 3 hours, to achieve optimum yields.

The catalyst can, for example, be present as a suspension in the reaction mixture in the form of powder through to broken pieces. Use of the catalyst in a fixed bed is a further possible way of carrying out the process.

After the reaction has ended, the catalyst can, if It was present in suspension, be separated off, for example filtered off, and the end product can be isolated by methods known per se, for example crystallization from a solvent such as methanol, isopropanol, methanol/water mixture, etc.

If necessary, the reaction mixture and/or the end product can be neutralized using an acid, e.g. formic acid, acetic acid, sulfuric acid, hydrochloric acid, etc.

The carboxylic esters and alcohols used in the process of the invention are known or can be obtained by methods known per se.

The invention further provides for the use of a tin(IV) compound comprising a radical of the formula

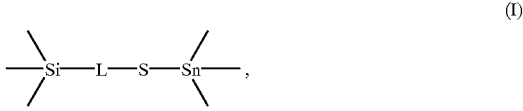

$$\text{—Si—L—S—Sn—} \quad (I)$$

bound to an inorganic support, where L is an at least divalent radical and at least one of the free valences of the Si in formula (I) is bound to the inorganic support, as catalyst in the transesterification of carboxylic esters.

The carboxylic esters prepared according to the invention are, for example, valuable antioxidants against oxidative, thermal or actinic degradation of sensitive organic materials. Such materials are, for example, synthetic polymers of functional liquids such as lubricants, hydraulic fluids or metalworking fluids, etc.

EXAMPLES

A) Immobilization of thiols and disulfides

All reactions are carried out under inert gas.

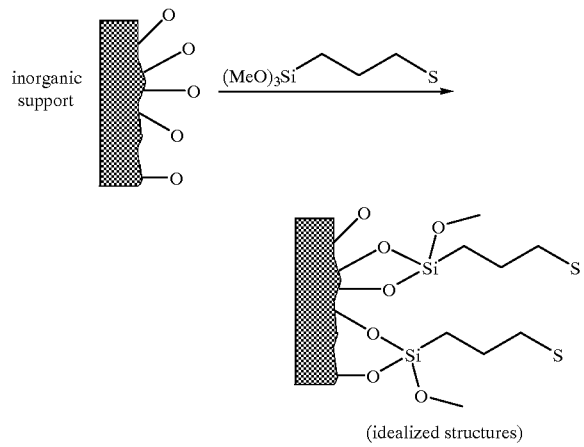

(idealized structures)

General procedure for immobilizing 3-mercaptopropyltrimethoxysilane. 100 g of support are stirred in 700 ml of toluene in an inert gas atmosphere and dried by distilling off 200–300 ml of toluene. After cooling to about 40° C., 40 ml (0.215 mol) of 3-mercaptopropyltrimethoxysilane are added, the mixture is again distilled briefly and subsequently stirred for 20 hours at 100°–110° C., ensuring that the methanol formed can distill off. After cooling, the support is filtered off, washed with 2×200 ml of each of ethyl acetate, methanol and hexane and finally dried under reduced pressure (1 mbar) at 70° C. for 15 hours.

Example A1

20 g of dried silica gel (Merck 100) (2 hours at 110° C. in a vacuum oven) are suspended in 80 ml of dried toluene in a flask fitted with a stirrer and treated with 10 g (51 mmol) of 3-mercaptopropyltrimethoxysilane (Fluka, purum). The mixture is stirred for 12 hours at 100° C. and the methanol formed is distilled off. The solid is then filtered off and washed 4 times with 100 ml of methanol. Finally, the functionalized silica gel is dried under reduced pressure at 70–100° C. This gives 22.4 g of product having an S content of 2.85%. This corresponds to a loading density of 0.89 mmol of thio compound per g of material.

Examples A2–A9 are carried out according to the above-described general procedure, giving the results shown in Table 1 for the corresponding variations.

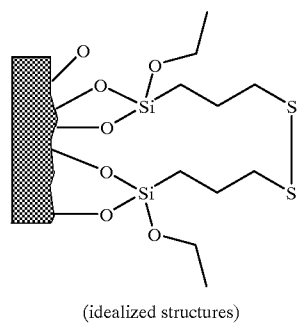

(idealized structures)

50 g of silica gel Merck 100 are stirred in 250 ml of toluene in an inert gas atmosphere and dried by distilling off about 50 ml of toluene. After cooling to about 40° C., 23.7 g (0.05 mol) of bis(3-triethoxysilylpropyl) disulfide are added, the mixture is again distilled briefly and subsequently stirred at 100°–110° C. for 20 hours, ensuring that the ethanol formed can distill off. After cooling, the support is filtered off, washed with 2×100 ml of each of ethyl acetate,

TABLE 1

| Ex. No. | Support | Preparation, deviation from the procedure described | Analysis of S content | Loading mmol S/g |
|---|---|---|---|---|
| A2 | Silica gel Merck 100 | Batch using only 20 g of support, drying of the silica gel not by azeotropic distillation in toluene but under reduced pressure (5 mbar) at 120° C. for 2 hours. Immobilization in 80 ml of toluene and 0.05 mol of 3-mercaptopropyltrimethoxy-silane. Washing only with methanol. | 2.85% | 0.89 |
| A3 | Silica gel Merck 100 | 0.260 mol of 3-mercaptopropyltrimethoxy-silane added. Washing only with methanol. | 2.33% | 0.73 |
| A4 | Silica gel, Grace 332 | As in procedure described | 1.65% | 0.52 |
| A5 | Silica gel, Grace 332 | Drying of the silica gel not by azeotropic distillation in toluene but in high vacuum (0.1 mbar) at 140° C. for 4 hours. | 0.75% | 0.234 |
| A6 and A7 | Silica gel, Grace 332 | After addition of 3-mercaptopropyltri-methoxysilane, 0.5 ml of methanesulfonic acid added. | 2.98% | 0.93 |
| A8 and A9 | Silica gel Merck 100 | 0.269 mol of 3-mercaptopropyltrimethoxy-silane added. Washing only with methanol. | 2.73% | 0.85 |

Example A10

Immobilization of bis(3-triethoxysilylpropyl) disulfide

The bis(3-triethoxysilylpropyl) disulfide is prepared by a method analogous to that described by W. Buder, Z. Naturforsch., 34b (1979) 790–793.

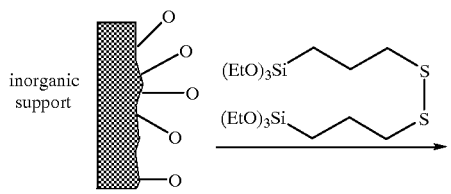

methanol and hexane and finally dried under reduced pressure (1 mbar) at 70° C. for 15 hours. This gives white material having an S content of 1.83%. This corresponds to a loading density of 0.29 mmol of disulfide per g.

B) Preparation of the fin(IV) catalysts

All reactions are carried out under inert gas.

Example B1

8 g of the thio compound fixed to silica gel from Example A1 are suspended in 60 ml of hexane, cooled to 0° C. and slowly treated with 5.12 g of an 18.1% solution of $SnCl_4$ in hexane. After 15 minutes, 0.8 g of triethylamine is added and the mixture is stirred for 2 hours at room temperature. Finally, the product is filtered off, washed first with hexane, then with a sodium carbonate solution and with water and then dried overnight under reduced pressure at 80° C. This gives 8.1 g of product having an S content of 2.7% and an Sn content of 2.46%. This corresponds to an Sn loading density of 0.201 mmol/g and a ratio of Sn to S of about 1:4.

Examples B2–B16

The results of the reaction of immobilized sulfur compounds with $SnCl_4$ and the variations of the experimental parameters are summarized in Table 2. (MW in kg means weight of product in kg per mol of Sn)

TABLE 2

Summary of the SnCl$_4$-S catalysts

| Cat. No. | Support-SH | Support | Remarks | Analysis S % | Analysis Sn % | S/Sn | MW kg |
|---|---|---|---|---|---|---|---|
| B2 | A2 | Merck 100 | | 2.7 | 2.46 | 4.1 | 4.8 |
| B3 | A3 | Merck 100 | | 2.24 | 3.25 | 2.55 | 3.64 |
| B4 | A6 | Grace 332 | | 2.75 | 3.34 | 3.1 | 3.57 |
| B5 | A6 | Grace 332 | | 2.8 | 3.28 | 3.2 | 3.63 |
| B6 | A6 | Grace 332 | | 2.83 | 3.1 | 3.4 | 3.84 |
| B7 | A6 | Grace 332 | | 2.71 | 2.57 | 3.9 | 4.63 |
| B8 | A6 | Grace 332 | | 2.84 | 2.01 | 5.3 | 5.96 |
| B9 | A6 | Grace 332 | | 2.74 | 3.88 | 2.63 | 3.07 |
| B10 | A6 | Grace 332 | | 2.78 | 3.44 | 3 | 3.46 |
| B11 | A5 | Grace 332 | | 0.72 | 1.06 | 2.53 | 11.2 |
| B12 | A8 | Merck 100 | | 2.42 | 3.8 | 2.37 | 3.13 |
| B13 | Integrated | Merck 100 | | 1.89 | 2.22 | 3.2 | 5.34 |
| B14 | A7 | Grace 332 | | 2.8 | 5.13 | 2.03 | 2.33 |
| B15 | A7 | Grace 332 | | 2.8 | 4.86 | 2.15 | 2.45 |
| B16 | A6 | Grace 332 | Coproportionation | 2.85 | 4.26 | 2.5 | 2.8 |

Et represents ethyl, Me represents methyl and Ac represents acetate.

Notes on Examples B2–B16.

B2: A solution of 0.93 g (3.56 mmol) of SnCl$_4$ in 4 ml of hexane is added at 0° C. to a suspension of 8 9 of the immobilized thiol from Example A2 (7.12 mmol of S) in 65 ml [lacuna] while stirring. After 15 minutes, 0.8 g of triethylamine is added, the mixture is stirred for 2 hours at room temperature, then filtered, washed first with hexane then with a sodium bicarbonate solution and finally with plenty of water. The white product is dried under reduced pressure (5 mbar) at 80° C. for 15 hours.

B3: A solution of 9.5 g (36 mmol) of SnCl$_4$ in 50 ml of hexane is added at 0° C. to a suspension of 100 g of the immobilized thiol from Example A3 (73 mmol of S) in 750 ml of hexane while stirring. After 15 minutes, 14.7 g (14.6 mmol) of triethylamine are added, the mixture is stirred for 2 hours at room temperature, then filtered. After washing (750 ml of hexane, 500 ml of acetone, 1 l of saturated sodium bicarbonate solution, 3 l of water, 250 ml of ethanol), the white product is dried under reduced pressure (5 mbar) at 80° C. for 15 hours.

B4: A solution of 2.4 g (9.3 mmol) of SnCl$_4$ in 10 ml of hexane is added at 0° C. to a suspension of 10 g of the immobilized thiol from Example A6 (9.3 mmol of S) in 50 ml of hexane while stirring. After 15 minutes, 1 g (10 mmol) of triethylamine is added, the mixture is stirred under reflux for 12 hours, cooled and filtered. After washing (50 ml each: 2×hexane, 2×methanol, 2×NaHCO$_3$ (2M), 3×water, 2×methanol, 2×ethyl acetate, 2×hexane), the white product is dried under reduced pressure (5 mbar) at 80° C. for 15 hours.

B5: Prepared the same way as B4, except that only 1.2 g (4.6 mmol) of SnCl$_4$ are added.

B6: Prepared the same way as B4, except that only 0.806 g (3.1 mmol) of SnCl$_4$ is added.

B7: Prepared the same way as B4, except that only 0.61 g (2.35 mmol) of SnCl$_4$ is added.

B8: Prepared the same way as B5, except that toluene is used in place of hexane as solvent for the reaction and that the reaction is completed at 100° C.

B9: Prepared the same way as B4, except that 2 g (20 mmol) of triethylamine are used.

B10: Prepared the same way as B5, except that an after-reaction time of only 2 hours at room temperature is employed.

B11: A solution of 0.62 g (2.4 mmol) of SnCl$_4$ in 10 ml of toluene is added at 0° C. to a suspension of 20 g of the immobilized thiol from Example A5 (4.7 mmol of S) in 120 ml of toluene while stirring. After 15 minutes, 0.5 g (5 mmol) of triethytamine is added, the mixture is stirred for 12 hours at 110° C., cooled and filtered. After washing (50 ml each: 2×hexane, 2×methanol, 2×NaHCO$_3$ (2M), 3×water, 2×methanol), the white product is dried under reduced pressure (5 mbar) at 80° C. for 15 hours.

B12: Prepared the same way as B3, except that the reaction is carried out starting from 100 g of immobilized thiol from Example A8 (85 mmol of S) in 600 ml of hexane, 42.5 mmol of SnCl$_4$ in 45 ml of hexane and 1.7 mol of triethylamine.

B13: Integrated immobilization of thiol and preparation of the Sn compound.

100 g of silica gel Merck 100 are stirred in 600 ml of toluene in an inert gas atmosphere and dried by distilling off 200 ml of toluene. After cooling to about 40° C., 25 ml (0.135 mol) of 3-mercaptopropyltrimethoxysilane and 0.2 ml of methanesulfonic acid are added, the mixture is again distilled briefly and subsequently stirred at 100°–110° C. for 20 hours, ensuring that the methanol formed can distill off. After cooling, the support is filtered off and washed with 2×200 ml of methanol. (A small sample is dried and analyzed→S content: 1.93%). Half of the methanol-moist material (30 mmol of S) is slurried in 150 ml of toluene and slowly treated while stirring at room temperature with 3.9 g (15 mmol) of $SnCl_4$ and subsequently with a freshly prepared sodium methoxide solution in methanol (30 mmol of sodium in 35 ml of methanol). The mixture is stirred for 4 hours at room temperature, then filtered, washed (2×100 ml each of methanol, $NaHCO_3$ 2M, water, methanol) and the product is dried under reduced pressure (5 mbar) at 80° C. for 15 hours.

B14: A solution of 1.2 g (4.6 mmol) of $SnCl_4$ is added at room temperature to a suspension of 10 g of the immobilized thiol from Example A7 (9.3 mmol of S) in 50 ml of methanol while stirring. After 15 minutes, 18.6 mmol of triethylamine are added, the mixture is stirred for 2 hours, filtered and washed (50 ml each: 2×water, 2×saturated $NaHCO_3$, 3×water, 3×methanol). The white product is dried under reduced pressure (5 mbar) at 80° C. for 15 hours.

B15: Prepared the same way as B14, except that sodium acetate is used in place of triethylamine.

B16: 0.31 g (1.2 mmol) of $SnCl_2$ is added at room temperature to a suspension of 5 g of the immobilized tin compound from Example B5 (4.4 mmol of S, 1.38 mmol of Sn) in 25 ml of toluene while stirring. The mixture is then stirred for 15 hours at 110° C., cooled and filtered. After washing (20 ml each: 2×hexane, 2×methanol, 2×$NaHCO_3$ (2M), 2×water, 2×methanol), the white product is dried under reduced pressure (5 mbar) at 70° C. for 15 hours. The tin content of the product is 30% higher than that of Example B5.

The results of the reaction of immobilized alkyl thiols with various Sn(IV) compounds and the various experimental conditions are summarized in Table 3.

TABLE 3

Summary of various Sn(IV) compounds Examples B17–29

| Cat. No. | Support-SH | Sn compound | Analysis S % | Analysis Sn % | S/Sn | MW kg |
|---|---|---|---|---|---|---|
| B17 | A4 | Bu2SnO | 1.51 | 4.11 | 1.36 | 2.9 |
| B18 | A4 | Ph2SnO | 1.48 | 3.35 | 1.65 | 3.57 |
| B19 | A4 | BuSnCl3 | 1.53 | 3.14 | 1.81 | 3.79 |
| B20 | A4 | BuSnCl3 | 1.51 | 2.68 | 2.01 | 4.44 |
| B21 | A4 | BuSnCl3 | 1.63 | 2.01 | 3.02 | 5.92 |
| B22 | A4 | PhSnCl3 | 1.46 | 2.62 | 2.1 | 4.55 |
| B23 | A4 | Bu3SnCl | 1.49 | 3.94 | 1.41 | 3.02 |
| B24 | A4 | Ph3SnOH | 1.41 | 4.46 | 1.18 | 2.57 |
| B25 | A4 | BuSnO)OH | 1.6 | 2.77 | 2.15 | 4.3 |
| B26 | A4 | 'Sn(OEt)4' | 1.6 | 3.44 | 1.72 | 3.0 |
| B27 | A6 | Bu2SnOAc | 2.72 | 4.26 | 2.37 | 2.8 |
| B28 | A6 | BuSn(OH)2Cl | 2.42 | 3.8 | 2.37 | 3.14 |
| B29 | A9 | BuSn(OH)2Cl | 2.54 | 4.36 | 2.17 | 2.75 |

Bu represents butyl, Ph represents phenyl, B17–B28: support, Grace 332; B29: support, Merck silica gel 100

B17, $Bu_2SnO$ 1 g (4 mmol) of dibutyltin oxide is added to a suspension of 10 g of the immobilized thiol from Example A4 (5.2 mmol of S) in 60 ml of toluene while stirring. The mixture is then heated and 10 ml of toluene are distilled off. After a total of 2.5 hours, the mixture is cooled to room temperature, filtered and washed (50 ml each: 2×hexane, 1×acetone, 3×water, 2×methanol, 2×ethyl acetate, 2×hexane). Finally, the white product is dried under reduced pressure (5 mbar) at 50° C. for 15 hours.

B18, $Ph_2SnO$ 1.15 g (4 mmol) of diphenyltin oxide are added to a suspension of 10 g of the immobilized thiol from Example A4 (5.2 mmol of S) in 60 ml of toluene while stirring. The mixture is then heated and 10 ml of toluene are distilled off. After a total of 7 hours, the mixture is cooled to room temperature, filtered and washed (50 ml each: 2×hexane, 1×acetone, 3×water, 2×methanol, 2>hexane). Finally, the white product is dried under reduced pressure (5 mbar) at 50° C. for 15 hours.

B19, $BuSnCl_3$

A solution of 1.69 g (6 mmol) of butyltin trichloride in 10 ml of hexane is added at 0° C. to a suspension of 10 g of the immobilized thiol from Example A4 (5.2 mmol of S) in 40 ml of hexane while stirring. After 15 minutes, 0.61 g (6 mmol) of triethylamine is added, the mixture is stirred under reflux for 3 hours, cooled and filtered. After washing (50 ml each: 2×hexane, 2×methanol, 2×$NaHCO_3$ (2M), 3×water, 2×methanol, 2×ethyl acetate, 2×hexane), the white product is dried under reduced pressure (5 mbar) at 50° C. for 15 hours.

B20, $BuSnCl_3$

Same as Example B19, except that 0.85 g (3 mmol) of butyltin trichloride is added.

B21, $BuSnCl_3$

Same as Example B19, except that 0.51 g (1.8 mmol) of butyltin trichloride is added.

B22, $PhSnCl_3$

Same as Example B19, except that 0.94 g (3 mmol) of phenyltin trichloride is added.

B23, $Bu_3SnCl$

Same as Example B19, except that 1.95 g (6 mmol) of tributyltin trichloride are added.

B24, $Ph_3SnOH$

A suspension of 2.2 g (6 mmol) of triphenyltin hydroxide in 20 ml of hexane is added at 0° C. to a suspension of 10 g of the immobilized thiol from Example A4 (5.2 mmol of S) in 40 ml of hexane while stirring. The mixture is briefly distilled and subsequently refluxed for 16 hours. It is then cooled and filtered. After washing (50 ml each: 2×hexane, 2×ethyl acetate, 2×methanol, 2×ethyl acetate, 2×hexane), the white product is dried under reduced pressure (5 mbar) at 50° C. for 15 hours.

B25, $BuSn(O)OH$ 0.56 g (2.6 mmol) of solid butyltin hydroxide oxide is added at 0° C. to a suspension of 10 g of the immobilized thiol from Example A4 (5.2 mmol of S) in 70 ml of hexane while stirring. The mixture is briefly distilled and subsequently refluxed for 16 hours. It is then cooled and filtered. After washing (50 ml each: 2×ethyl acetate, 2×methanol, 2×ethyl acetate, 2×hexane), the white product is dried under reduced pressure (5 mbar) at 60° C. for 15 hours.

B26, $SnCl_4/NaOEt$ 10 mmol of sodium ethoxide freshly prepared from sodium and ethanol are slurried in 50 ml of toluene. 0.65 g (2.5 mmol) of tin tetrachloride are then added at 0° C. 10 g of the immobilized thiol from Example A4 (5.2 mmol of S) are added at room temperature to the resulting solution, the mixture is briefly distilled and refluxed for 3 hours. After washing (50 ml each: 2×water, 2×methanol, 2×ethyl acetate, B27, Bu$_2$Sn(OAc)$_2$ 1.51 g (4.3 mmol) of dibutyltin diacetate are added at 0° C. to a suspension of 10 g of the immobilized thiol from Example A6 (9.3 mmol of S) in 60 ml of toluene while stirring. The mixture is then heated, 15 ml of toluene are distilled off and the mixture is subsequently stirred for 15 hours at 110° C. It is then cooled to room temperature, filtered and washed (50 ml each: 2×hexane, 1×acetone, 2×methanol, 2×water, 2×methanol, 2×ethyl acetate, 2×hexane) and the white product is dried under reduced pressure (5 mbar) at 70° C. for 15 hours.

B28, BuSn(OH)$_2$Cl

Same as B27, except that 1.2 g of butyltin chloride dihydroxide are added and washing is carried out as follows: 50 ml each: 2×methanol, 2×ethyl acetate, 2×hexane.

B29, BuSn(OH)$_2$Cl 5.15 g (21 mmol) of butyltin chloride dihydroxide are added at room temperature to a suspension of 50 g of the immobilized thiol from Example A9 (42 mmol of S) in 300 ml of toluene while stirring. The mixture is then heated, about 40 ml of toluene are distilled off and the mixture is subsequently stirred for 15 hours at 110° C. It is then cooled to room temperature, filtered and washed (250 ml each: 3×methanol, 2×ethyl acetate, 2×hexane) and the white product is dried under reduced pressure (5 mbar) at 70° C. for 15 hours.

Immobilization of Sn(IV)-S compounds having trialkoxysilane radicals

Preparation of the Sn(IV)-S compounds having trialkoxysilane radicals

B30 Preparation of (Bu)$_2$Sn[S(CH$_2$)$_3$Si(OCH$_3$)$_3$]$_2$

2 HS(CH$_2$)$_3$Si(OCH$_3$)$_3$+(Bu)$_2$SnCl$_2$+2(C$_2$H$_5$)$_3$N→(Bu)$_2$Sn[S(CH$_2$)$_3$Si(OCH$_3$)$_3$]$_2$+2(C$_2$H$_5$)$_3$N*HCl 98.2 g (0.50 mol) of 3-mercaptopropyltrimethoxysilane and 52.6 g (0.52 mol) of triethylamine together with 200 ml of n-hexane are placed in a reaction vessel. Subsequently, a solution of 76.0 g (0.25 mol) of dibutyltin dichloride in 300 ml of n-hexane is metered in over a period of about 20 minutes and the reservoir is rinsed with 200 ml of n-hexane. The internal temperature rises from 20 to 35° C. during this step. A white solid starts to precipitate right at the beginning of the metered addition. After stirring for 24 hours at about 20° C., the precipitate is filtered off, the filtrate and the residues are washed with 200 ml of n-hexane. The still slightly turbid filtrates are combined and evaporated in a double-wall reactor to a temperature of about 61° C. and 1 hPa, which results in disappearance of the turbidity. At 20° C., about 143 g of a slighty yellowish, liquid product are drained off (91.8% of theory). Microanalysis: S 10.44%, Sn 19.2%.

B31 Preparation of (Bu)$_2$SnCl[S(CH$_2$)$_3$Si(OCH$_3$)$_3$]

(Bu)$_2$Sn[S(CH$_2$)$_3$Si(OCH$_3$)$_3$]$_2$+(Bu)$_2$SnCl$_2$→2(Bu)$_2$SnCl[S(CH$_2$)$_3$Si(OCH$_3$)$_3$]

In a test tube, 24.3 g (0.080 mol) of tributyitin dichloride are dissolved in 49.9 g (0.080 mol) of the compound from Example B30 while warming gently (about 50° C.) and allowed to stand for 2 days at room temperature. Microanalysis: S 6.29%, Sn 26.5%

B32 Preparation of (Ph)$_2$Sn[S(CH$_2$)$_3$Si(OCH$_3$)$_3$]$_2$

2 HS(CH$_2$)$_3$Si(OCH$_3$)$_3$+(Ph)$_2$SnCl$_2$+2(C$_2$H$_5$)$_3$N→(Ph)$_2$Sn[S(CH$_2$)$_3$Si(OCH$_3$)$_3$]$_2$+2(C$_2$H$_5$)$_3$N*HCl

Method of preparation analogous to Example B30 except that 86 g (0.25 mol) of diphenyltin dichloride are used in place of dibutyltin dichloride. The liquid product is obtained in a yield of 87.5%. Microanalysis: S 10.12%, Sn 17.1%

B33 Preparation of Sn[S(CH$_2$)$_3$Si(OCH$_3$)$_3$]$_4$

4 HS(CH$_2$)$_3$Si(OCH$_3$)$_3$+SnC$_4$+4(C$_2$H$_5$)$_3$N Sn[S(CH$_2$)$_3$Si(OCH$_3$)$_3$]$_4$+4(C$_2$H$_5$)$_3$N*HCl 98.2 g (0.50 mol) of 3-mercaptopropyltrimethoxysilane and 50.6 g (0.50 mol) of triethylamine together with 200 ml of n-hexane are placed in a reaction vessel. Subsequently, a solution of 32.6 g (0.125 mol) of tin tetrachloride in 250 ml of n-hexane is metered in over a period of about 45 minutes. The further procedure is the same as in Example B30. The liquid product is obtained in a yield of 85.1%. Microanalysis: S 12.2%, Sn 14.5%

B34 Preparation of SnCl$_{4-n}$[S(CH$_2$)$_3$Si(OCH$_3$)$_3$]$_n$

Sn[S(CH$_2$)$_3$Si(OCH$_3$)$_3$]$_4$+SnCl$_4$→2SnCl$_{4-n}$[S(CH$_2$)$_3$Si(OCH$_3$)$_3$]$_n$ 40.0 g (0.044 mol) of the compound from Example B33 are placed in an argon-blanketed test tube and 11.6 g (0.044 mol) of tin tetrachloride are stirred in. The reaction is exothermic and a white solid is precipitated. Microanalysis: liquid part of the mixture: S 12.3%, Sn 14.5%; solid part: S 10.24%, Sn 21.8%.

B35: Immobilization of the compound from Example B30 1412/21

(Bu)$_2$Sn[S(CH$_2$)$_3$Si(OCH$_3$)$_3$]$_2$

A suspension of 40 g of silica gel Merck 100 in 300 ml of toluene is first dried by azeotropic distillation of 100 ml of toluene. After cooling to room temperature, 31.2 g of the tin compound 1412/21 are added, the mixture is briefly distilled and stirred for 18 hours at 100° C., ensuring that the alcohol formed can distill off. After cooling, the product is filtered off, washed (100 ml each: 3×methanol, 3×ethyl acetate, 3×hexane) and dried under reduced pressure (5 mbar) at 70° C for 15 hours.

B36: Immobilization of the compound from Example B32 (Ph)$_2$Sn[S(CH$_2$)$_3$Si(OCH$_3$)$_3$]$_2$. Prepared the same way as in Example B35, except that the reaction is carried out using 33.7 g of the Sn compound from Example B32.

B37: Immobilization of the compound from Example B31 (Bu)$_2$SnCl[S(CH$_2$)$_3$Si(OCH$_3$)$_3$]. Prepared the same way as in Example B35, except that the reaction is carried out using 23.1 g of the Sn compound from Example B31 and that washing is carried out as follows: 100 ml each: 3×methanol, 1×NaHCO$_3$ 1M, 3×water, 3×methanol, 2×ethyl acetate, 2×hexane.

B38: Immobilization of the compound from Example B34 SnCl$_{4-n}$[S(CH$_2$)$_3$Si(OCH$_3$)$_3$]$_n$. Prepared the same way as in Example B35, except that the reaction is carried out using 29 g of the Sn compound B34 and that washing is carried out as follows: 100 ml each: 3×methanol, 1×NaHCO$_3$ 1 M, 3×water, 3×methanol, 2×ethyl acetate, 2×hexane.

The results are summarized in Table 4.

TABLE 4

Immobilization of Sn(IV)-S compounds having trialkoxysilane radicals

| Cat. No. | Support | Sn compound No. | Sn compound | Analysis S % | Analysis Sn % | S/Sn | MW kg |
|---|---|---|---|---|---|---|---|
| B35 | Merck 100 | B30 | ((MeO)$_3$Si—C$_3$H$_6$—S)$_2$SnBu$_2$ | 1.94 | 4.2 | 1.72 | 2.84 |
| B36 | Merck 100 | B32 | ((MeO)$_3$Si—C$_3$H$_6$—S)$_2$SnPh$_2$ | 2.36 | 3.86 | 2.28 | 3.01 |
| B37 | Merck 100 | B31 | ((MeO)$_3$Si—C$_3$H$_6$—S)Sn(Bu)$_2$Cl | 2.16 | 4.4 | 1.82 | 2.71 |
| B38 | Merck 100 | B34 B | ((MeO)$_3$Si—C$_3$H$_6$—S)$_n$SnCl$_{4-n}$ | 4.58 | 3.48 | 4.9 | 3.35 |

Me represents methyl, Ph represents phenyl and Bu represents butyl

Preparation of Sn—S compounds by sol-gel processes

Sol-gel processes are described, for example, in the following publications:

C. J. Brinker, G. W. Scherrer, book: Sol Gel Science, Academic Press (1990).

L. L. Hench and J. K. West, Chem. Rev., 90 (1990) 33–72.

U. Schubert et al., J. Non Cryst. Solids, 105 (1988) 165–170.

P. Panster, CLB Chemie in Labor und Biotechnik, 43 (1992) 16–21.

These processes can be used in an analogous way for the immobilization of the catalysts of the invention. Examples B39 and 40 illustrate this.

B39 5.42 g (6 mmol) of ((CH$_3$O)$_3$Si—C$_3$H$_6$—S)$_4$Sn (compound from Example B33), 7.3 g (48 mmol) of tetramethoxysilane, 1.56 g (6 mmol) of tin tetrachloride and 100 ml of acetone are combined while stirring in a flask. 34 ml of a 2.8N phosphoric acid solution are added dropwise to the above solution over a period of 30 minutes. The resulting solution is allowed to stand for 4 days in an open vessel, resulting in evaporation of the acetone and formation of a yellowish-white mass. This is stirred for 14 hours in 200 ml of water, filtered off, washed (30 ml each: 3×methanol, 1×NaHCO$_3$ 2M, 3×water, 3×methanol, 2×ethyl acetate, 2×hexane) and dried under reduced pressure (5 mbar) at 70° C. for 15 hours.

B40 2.83 g of triethylamine are added to a solution of 7.92 g (52 mmol) of tetramethoxysilane, m 0.94 g (4 mmol) of n-octyltrimethoxysilane, 2.75 g (14 mmol) of 3-mercaptopropyltrimethoxysilane, 100 ml of acetone and 1.82 g (7 mmol) of tin tetrachloride, resulting in formation of a white precipitate. 35 ml of a 2.8N phosphoric acid solution are added dropwise to this mixture over a period of 30 minutes. The resulting clear solution is allowed to stand for 6 days in an open vessel, resulting in evaporation of the acetone and formation of a yellowish-white mass. This is partially dried overnight at 70° C. under reduced pressure (5 mbar), washed (50 ml each: 3×methanol, 1×NaHCO$_3$ 2M, 3×water, 3×methanol, 2×ethyl acetate, 2×hexane) and dried under reduced pressure (5 mbar) at 70° C. for 15 hours.

The results are summarized in Table 5.

TABLE 5

Sn catalysts prepared by sol-gel processes

| Cat. No. | Composition | Analysis S % | Analysis Sn % | S/Sn | MW kg |
|---|---|---|---|---|---|
| B39 | ((MeO)$_3$Si—C$_3$H$_6$—S)$_4$Sn, SnCl$_4$, (MeO)$_4$Si | 6.62 | 10.4 | 2.64 | 1.28 |
| B40 | (MeO)$_3$Si—C$_3$H$_6$—SH, SnCl$_4$, (MeO)$_4$Si, n-Octyl-Si(OMe)$_3$ | 5.1 | 7.45 | 2.55 | 1.6 |

Me represents methyl

Immobilization of Sn—S compounds on disulfides bound to supports

B41 8 g of a material (Deloxan® DSP from Degussa) prepared as described in the literature (U. Deschier et al., Angew. Chemie., 98 (1986) 237–53; P. Panster, CLB Chemie in Labor und Biotechnik, 43 (1992) 16–21) by copolycondensation of bis(3-trialkoxysilylpropyl) disulfide and having a sulfur content of 19.7% are dried in 50 ml of toluene by azeotropic distillation of 20 ml of toluene. After cooling, a solution of 1.68 g (3.69 mmol) of Sn(N(SiCH$_3$)$_2$)$_2$ in 15 ml of toluene is added dropwise at room temperature. The mixture is then stirred for 15 hours at 70° C. and for another 2 hours at 120° C. After cooling to room temperature, it is filtered, washed (30 ml each: 3×methanol, 1×NaHCO$_3$ 2M, 3×water, 3×methanol, 2×ethyl acetate, 2×hexane) and dried under reduced pressure (5 mbar) at 70° C. for 15 hours.

B42 10 g of the disulfide bound to silica gel from Example A10 in 70 ml of toluene are dried by azeotropic distillation of 40 ml of toluene. After cooling, a solution of 1.26 g (2.85 mmol) of Sn(N(SiCH$_3$)$_2$)$_2$ in 10 ml of toluene is added dropwise at room temperature. The further procedure is analogous to Example B41.

B43 Reduction of the disulfide to thiol: 90 ml of methanol, 10 ml of 1,4-dioxane, 10 ml of water, 5 g of triphenylphosphine and 1 ml of methanesulfonic acid are added to 16 g of the disulfide described in PU732.1 and the mixture is stirred at 70° C. for 17 hours. Subsequently, the product is filtered off and washed with 700 ml of methanol/toluene. Reaction with SnCl$_4$: 0.74 g of sodium acetate is added while stirring to half of the moist product in 30 ml of methanol and, subsequently, 1.04 g of tin tetrachloride are slowly added. After 2 hours, the mixture is filtered and washed (40 ml each: 1×MeOH, 1×H$_2$O, 2×NaHCO$_3$ 2M, 3×water, 3×MeOH) and dried under reduced pressure (5 mbar) at 70° C. for 15 hours.

from Example B3 are added to this melt. The apparatus is evacuated to 3 mbar, the contents are stirred at 180° C. for 4 hours and the methanol formed is continuously distilled off. Subsequently, the mixture is cooled to 150° C. and filtered. Reuse: The unwashed catalyst can be reused as described above.

TABLE 6

Sn catalysts based on immobilized dialkyl disulfides

| Cat. No. | Support | Immob. disulfide | Sn compound | Analysis S % | Analysis Sn % | S/Sn | MW kg |
|---|---|---|---|---|---|---|---|
| B41 | Deloxan | DSP | Sn(N(SiCH$_3$)$_2$)$_2$ | 18.39 | 4.28 | 16 | 2.8 |
| B42 | Merck 100 | A10 | Sn(N(SiCH$_3$)$_2$)$_2$ | 1.64 | 2.86 | 2.14 | 4.17 |
| B43 | Deloxan reduced | DSP | SnCl$_4$ | 17.93 | 5.34 | 12.5 | 2.23 |

C) Use Examples

Example C1

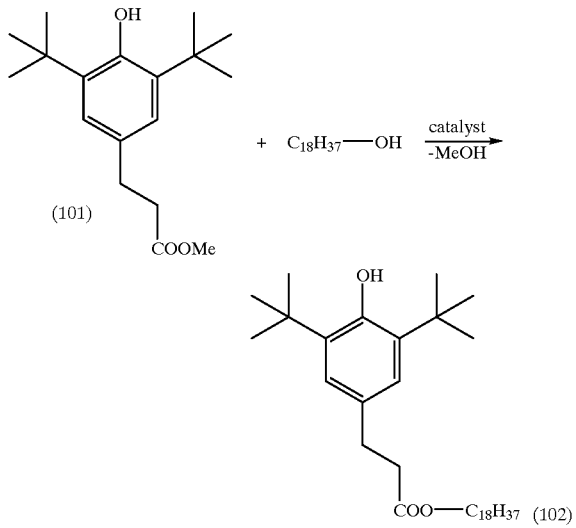

17.5 g of compound (101) (60 mmol) and 13.5 g of stearyl alcohol (50 mmol) are melted at 120° C. in a rotary evaporator. 2 g of the catalyst from Example B1 are then added and, under reduced pressure (100 mbar), the temperature is increased to 190° C. over a period of 30 minutes. The vacuum is then improved to 8 mbar over a period of 1 hour 20 minutes. After a further 30 minutes, the melt is then filtered and the catalyst is reused. In 4 reuses of the catalyst, a conversion of 85–90% according to GC is obtained in each case and the product in each case contains less than 1 ppm of Sn.

Example C2

142.6 g (0.489 mol) of compound (101) and 120.35 g (0.445 mol) of stearyl alcohol are placed in a sulfation flask and heated to 180° C. under inert gas. 15.39 g of catalyst Results:

| Catalyst use | Conversion based on stearyl alcohol used (GC) | ppm of tin in crude product |
|---|---|---|
| Fresh cat. | 76.8% | 2 |
| 1st reuse | 95.8% | <1 |
| 2nd reuse | 98.2% | 1 |
| 3rd reuse | 99.6% | <1 |
| 4th reuse | 99.9% | <1 |
| 5th reuse | 99.5% | <1 |

In all cases the selectivity is greater than 99%. The transmission at 425 nm is over 99% in all reuses.

The catalyst is still active even after the 5th reuse.

Example C3

The procedure is the same as described in Example C2. Batch size: 30.2 g (0.111 mol) of compound (101), 25.6 g (0.101 mol) of stearyl alcohol, 2.79 g of catalyst from Example B12.

Results:

| Catalyst use | Conversion based on stearyl alcohol used (GC) | ppm of tin in crude product |
|---|---|---|
| Fresh cat. | 61.4% | 2 |
| 1st reuse | 89.9% | 1 |
| 2nd reuse | 98.6% | <1 |
| 3rd reuse | 95.6% | 1 |
| 4th reuse | 97.5% | 2 |
| 5th reuse | 97.5% | <1 |

In all cases, the selectivity is greater than 99%. The transmission at 425 nm is above 99% in all reuses.

The catalyst is still active even after the 5th reuse.

Example C4

The procedure is the same as for Mu19. Batch size: 30.2 g (0.111 mol) of compound (101), 25.6 g (0.101 mol) of stearyl alcohol, 1.28 g of catalyst from Example B17.

Results:

| Catalyst use | Conversion based on stearyl alcohol used (GC) | ppm of tin in crude product |
|---|---|---|
| Fresh catalyst | 75.5% | 8 |
| 1st reuse | 91.1% | 5 |

In all cases, the selectivity is greater than 99%. The transmission at 425 nm is above 99% in the reuse.

The catalyst is still active even after the 1st reuse.

Example C5

The procedure is the same as that described in Example C2. Batch size: 33 g (0.12 mol) of compound (1019), 25.5 g (0.101 mol) of stearyl alcohol, 2.18 g of catalyst from Example B20.

Results:

| Catalyst use | Conversion based on stearyl alcohol used (GC) | ppm of tin in crude product |
|---|---|---|
| Fresh catalyst | 87.5% | 8 |
| 1st reuse | 78.5% | 10 |

In all cases, the selectivity is greater than 99%. The transmission at 425 [lacuna] is above 96%.

Example C6

The procedure is the same as that described in Example C2. Batch size: 30.2 g (0.111 mol) of compound (101), 25.6 g (0.101 mol) of stearyl alcohol, 1.26 g of catalyst from Example B28.

Results:

| Catalyst use | Conversion based on stearyl alcohol used (GC) | ppm of tin in crude product |
|---|---|---|
| Fresh catalyst | 98.7% | 4 |
| 1st reuse | 99.4% | <2 |

In all cases, the selectivity is greater than 99%. The transmission at 425 nm is above 99% in the reuse.

The catalyst is still active even after the 1st reuse.

Example C7

The procedure is the same as that described in Example C2. Batch size: 30.2 g (0.111 mol) of compound (101), 25.6 g (0.101 mol) of stearyl alcohol, 1.1 g of catalyst from Example B25.

Results:

| Catalyst use | Conversion based on stearyl alcohol used (GC) | ppm of tin in crude product |
|---|---|---|
| Fresh catalyst | 62.8% | 2 |
| 1st reuse | 82.1% | 1 |

In all cases, the selectivity is greater than 99%. The transmission at 425 nm is above 99% in the reuse.

The catalyst is still active even after the 1st reuse.

Example C8

The procedure is the same as that described in Example C2. Batch size: 129.7 g (0.445 mol) of compound (101), 120.4 g (0.445 mol) of stearyl alcohol, 2.9749 g of catalyst from Example B35.

Results:

| Catalyst use | Conversion based on stearyl alcohol used (GC) | ppm of tin in crude product |
|---|---|---|
| Fresh catalyst | 92.9% | 28 |
| 1st reuse | 96% | 17 |

In all cases, the selectivity is greater than 99%. The transmission at 425 nm is above 99% in the reuse.

The catalyst is still active even after the 1st reuse.

Example C9

The procedure is the same as that described in Example C2. Batch size: 30.2 9 (0.111 mol) of compound (101), 25.6 9 (0.101 mol) of stearyl alcohol, 1.24 g of catalyst from Example B41.

Results:

| Catalyst use | Conversion based on stearyl alcohol used (GC) | ppm of tin in crude product |
|---|---|---|
| Fresh catalyst | 99.7% | <1 |
| 1st reuse | 98.5% | 1 |

In all cases, the selectivity is greater than 99%. The transmission at 425 nm is above 99% in the reuse.

The catalyst is still active even after the 1st reuse.

Example C10

The procedure is the same as that described in Example C2. Batch size: 30.2 g (0.111 mol) of compound (101), 25.6 g (0.101 mol) of stearyl alcohol, 3.72 g of catalyst from Example B42.

Results:

| Catalyst use | Conversion based on stearyl alcohol used (GC) | ppm of tin in crude product |
|---|---|---|
| Fresh catalyst | 85.2% | 5 |
| 1st reuse | 86.7% | 5 |

In all cases, the selectivity is greater than 99%. The transmission at 425 nm is above 98%.

The catalyst is still active even after the 1st reuse.

Example C11

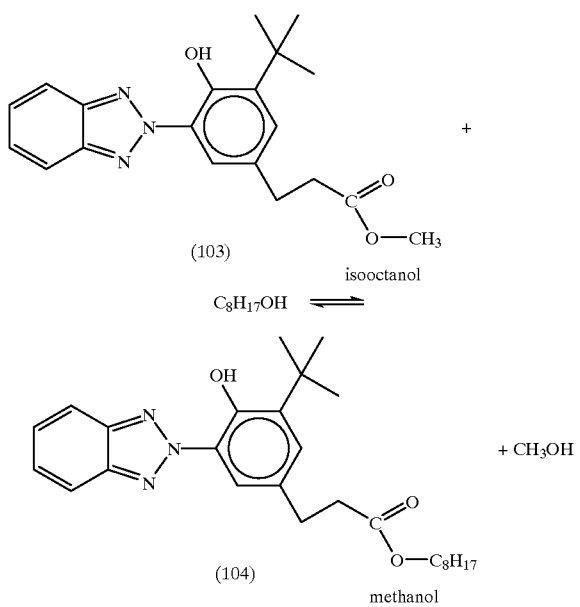

The catalyst described in Example B3 is used for the above transesterification. 4.0 g of catalyst, 100 g of compound (103) and 73.7 g of isooctanol isomer mixture are placed in a stirred glass reactor provided with a reflux condenser heated to 80° C. and a vacuum pump. The reactor is subsequently evacuated to 400 mbar and the reaction mixture is heated to reflux temperature while stirring. The methanol formed in the reaction is distilled off through the reflux condenser heated to 80° C. and is condensed in a downstream cold trap. After about 4 hours, a boiling temperature of the reaction mixture of 180–185° C. is reached. After further reaction for 3 hours, a conversion of 99.8% at a selectivity of almost 100% in respect of the initially charged methyl ester is achieved. After cooling the reaction mixture to 120° C., the catalyst is filtered off and reused in the next 2 reaction batches. Here, the filtered-off, unwashed catalyst is again mixed with 100 g of methyl ester, compound (103) and 73.7 g of isooctanol and the reaction is carried out using the above procedure. A conversion of 99.6% is achieved after only 5 hours. The selectivity is likewise almost 100%. The residual tin content of the product is 30 ppm both in the first test and also in the 2 recycling tests.

Example C12

Preparation of tetrakis[3-(3,5-di-tert-butyl-4-hydroxyphenyl)propionyloxymethyl]methane compound (105)

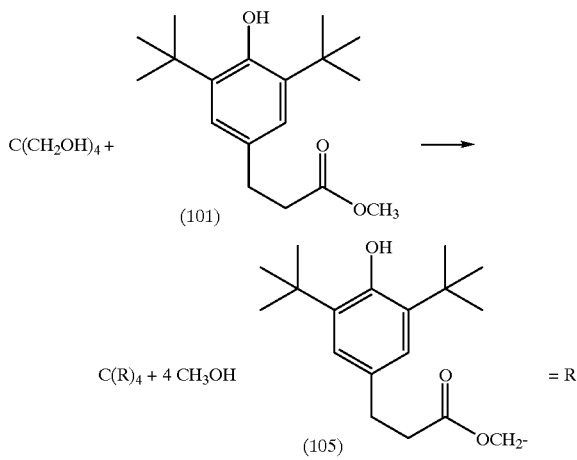

250.0 g (0.856 mol) of methyl 3,5-bis(1,1-dimethyl)-4-hydroxyphenylpropionate [sic] (101), 23.3 g (0.171 mol) and 5.12 g of catalyst from Example 829 are heated to 180° C. and held at this temperature for 6.5 hours. During this time, the pressure is gradually reduced to 3 mbar. 15.2 g (0.47 mol, 70% of theory) of the reaction product (105) are obtained. The catalyst is recovered by filtration. A clear, colorless product is obtained.

Example C13

Transesterification of a glyceride mixture with methyl 3,5-bis(1,1-dimethyl)-4-hydroxyphenyl-propionate [sic] (101)

65.0 g of coconut oil (about 0.096 mol), 50.9 g of glycerol 86.6% (0.48 mol), 292.4 g of methyl 3,5-bis(1,1-dimethylethyl)-4-hydroxyphenylpropionate (101) (1.00 mol) and 8.0 g of catalyst from Example B29 are slowly heated while stirring to 200° C. in a 1 liter flask provided with a dephlegmator at 60° C., a condenser at 15–20° C. and a cold trap at −80° C., with a pressure of 200 mbar being set. The temperature is held at 200° C. for two hours and the pressure is reduced from 200 mbar to 20 mbar over a period of one hour. 6.6 g of water and 30.0 g of methanol are taken off. The catalyst is recovered by filtration. 343.4 g of product are obtained as a clear, yellowish resin.

What is claimed is:

1. A process for the preparation of a compound of formula X

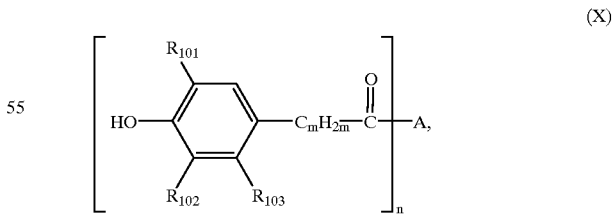

in which $R_{101}$ and $R_{102}$ are identical or different and are H, alkyl having from 1 to 18 C atoms, phenyl, $C_1$–$C_4$alkyl-substituted phenyl, phenylalkyl having from 7 to 9 C atoms, $C_5$–$C_{12}$cycloalkyl, $C_1$–$C_4$alkyl-substituted $C_5$–$C_{12}$cycloalkyl or a radical

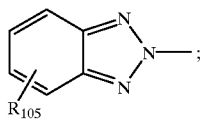

$R_{103}$ is H;
$R_{105}$ is H, Cl, —SO$_3$H or $C_1$–$C_4$alkyl;
m is 0, 1, 2 or 3; and
n is 1, 2, 3 or 4;
where,
when n=1,
A is —OR$_{104}$; and
$R_{104}$ is alkyl having from 2 to 45 C atoms, $C_2$–$C_{45}$alkyl interrupted by one or more oxygen, cycloalkyl having from 5 to 12 C atoms, alkenyl having from 2 to 18 C atoms, —CH$_2$CHOHCH$_2$OC(O)R$_{109}$ or —CH$_2$CH$_2$—OR$_{106}$; and
$R_{109}$ is H, alkyl having from 1 to 8 C atoms, alkenyl having from 3 to 6 C atoms or benyl; where
$R_{106}$ is

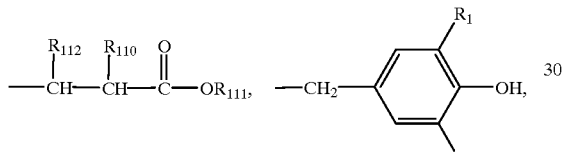

H, alkyl having from 1 to 24 C atoms, phenyl, cycloalkyl having from 5 to 12 C atoms or

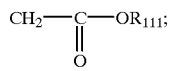

and
$R_{110}$ is H or —CH$_3$;
$R_{111}$ is H or alkyl having from 1 to 24 C atoms; and
$R_{112}$ is H or —CH$_3$, with the proviso that $R_{110}$ and $R_{112}$ are not simultaneously —CH$_3$; or, when n=2,
A is —O—C$_x$H$_{2x}$—O—, —O—(CH$_2$CH$_2$O)$_a$CH$_2$CH$_2$O— or —O—CH$_2$=CHCH$_2$—O—; in which
a Is from 1 to 30; and
x is from 2 to 20;
or, when n=3,
A is

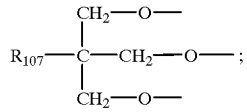

in which
$R_{107}$ is alkyl having from 1 to 24 C atoms or phenyl, or, when n=4,
A is

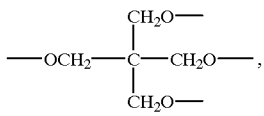

by transesterification of the corresponding lower alkyl ester with a higher alcohol or polyol
which comprises
reacting a compound of formula Xa

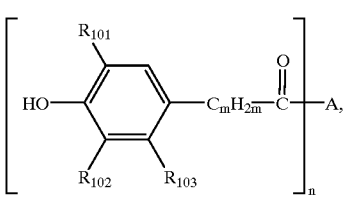

(Xa)

where A is —O-methyl,
with a higher alcohol or polyol of the formula

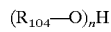

$(R_{104}—O)_nH$ at a reduced pressure (3 mbar to 400 mnbar) and at a temperature of 80–200° C. in the presence of an effective catalyzing amount of an immobilized in(IV) catalyst or mixture thereof obtained by reaction of a compound of formula (IIa)

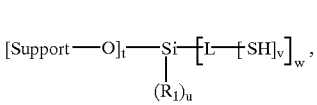

(IIa)

in which
t is 1, 2 or 3;
u is 0, 1 or 2;
v is 2,
w is 1, 2 or 3;
with the proviso that t+u+w=4;
L is $C_1$–$C_{18}$alkylene, $C_2$–$C_{18}$alkenylene or phenylene;
$R_1$ are, independently of one another, $C_1$–$C_4$alkoxy, phenoxy, $C_1$–$C_4$alkyl, phenyl or halogen; and
Support is an inorganic material selected from the group consisting of SiO$_2$, TiO$_2$, ZrO$_2$, MgO, NiO, WO$_3$, Al$_2$O$_3$, La$_2$O$_3$, silica gels, clays and zeolite; with a compound of formula IIb

Sn(R$_2$)$_4$ (IIb)

wherein
$R_2$ are, independently of one another, $C_1$–$C_{18}$alkyl, substituted $C_1$–$C_{18}$alkyl, $C_2$–$C_{18}$alkenyl, $C_1$–$C_{18}$haloalkyl, $C_6$–$C_{16}$haloaryl, $C_3$–$C_3$–$C_{16}$haloheteroaryl $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_{12}$hydroxyalkyl, $C_3$–$C_8$cycloalkyl, $C_6$–$C_{16}$aryl, substituted $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, —Cl, —Br, —I, OH, —$OC_1$–$C_{16}$alkyl, —$OC_6$–$C_{16}$aryl, —OOC—$C_1$–$C_{18}$alkyl, —OOC-phenyl, SH, —$N(Si(CH_3)_3)_2$, $SC_1$–$C_{18}$alkyl; —$SC_6$–$C_{16}$aryl, —SC(O)—$C_1$–$C_{18}$alkyl, —SC(O)-phenyl, —SC(S)—$C_1$–$C_{18}$alkyl, —SC(S)-phenyl, H or an oxygen bridge to a further Sn atom;

or two radicals $R_2$ are together =S or =O, with the proviso that at least one $R_2$ radical which can react with an SH group to form an S—Sn bond is present.

2. Process according to claim 1 for preparing compounds of the formula (X) in which n is one;

$R_{101}$ is tert-butyl or

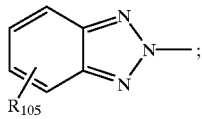

$R_{102}$ is tert-butyl;
$R_{103}$ and $R_{105}$ are H;
m is 2; A is $OR_{104}$;
$R_{104}$ is $(CH_2)_{17}CH_3$, $C_8H_{17}$ (isomer mixture), $C_2$–$C_{45}$alkyl interrupted by one or more oxygen, —$CH_2CHOHCH_2OC(O)R_{109}$; and
$R_{109}$ is alkenyl having from 3 to 5 C atoms;

or n is 2;

$R_{101}$ is tert-butyl or

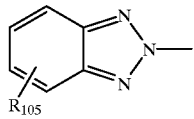

$R_{102}$ is $CH_3$;
$R_{103}$ is H;
m is 2;
A is —O—$(CH_2CH_2O)_aCH_2CH_2O$—; and
a is from 1 to 30;

or n is 3;

$R_{101}$ and $R_{102}$ are tert-butyl;
$R_{103}$ is H;
m is 2; and
A is —$O$—$CH_2$—CH(O—)—$CH_2$—O—;

or n is 4;

$R_{101}$ and $R_{102}$ are tert-butyl;
$R_{103}$ is H;
m is 2; and
A is $C(CH_2$—O—$)_4$.

* * * * *